United States Patent [19]

Abdulla

[11] Patent Number: 4,670,437
[45] Date of Patent: Jun. 2, 1987

[54] ANTIVIRAL PYRIDAZINE HYDRAZONES

[75] Inventor: Riaz F. Abdulla, Greenfield, Ind.

[73] Assignee: Eli Lilly and Company, Indianapolis, Ind.

[21] Appl. No.: 774,629

[22] Filed: Sep. 11, 1985

[51] Int. Cl.$^4$ .................... A61K 31/50; C07D 401/12; C07D 403/12; C07D 405/12
[52] U.S. Cl. .................... 514/247; 514/252; 514/253; 544/238; 544/239
[58] Field of Search ............... 544/238, 239; 514/252, 514/253, 247

[56] References Cited

PUBLICATIONS

Schauer et al., *Proc. Int. Conf. Chemotherapy*, 72, 329–331 (1972)
Likar et al., *J. Med. Chem.*, 14, 246 (1971).
Japelj et al., *Il. Farmaco. Ed. Sci.*, 28, 116 (1973).
Steiner et al., *J. Med. Chem.*, 24, 59 (1981).
Matyus et al., *Acta Chim. Acad. Sci. Hung.*, 106, 205 (1981).
Shams et al., *Ind. J. Chem.*, 21B, 317 (1982).
How et al, *Chem. Abs.*, 85, 192643m (1976).
Miyazawa, *Chem. Abs.* 63, 3477e (and index sheet).

*Primary Examiner*—Mark L. Berch
*Attorney, Agent, or Firm*—Bruce J. Barclay; Leroy Whitaker

[57] ABSTRACT

This invention provides antiviral pyridazinyl hydrazones of the formula

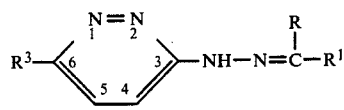

wherein when taken singly, R is H, CH$_3$ or C$_2$H$_5$; and R$^1$ is thienyl, halothienyl, pyridyl, methylthienyl, furyl, indolyl, tolyl, xylyl, biphenyl, C$_1$–C$_4$ alkoxyphenyl, 1-adamantyl and, when R is other than H, methyl; R and R$^1$ taken together form a 2-adamantindinyl group; and R$^3$ is a C$_4$–C$_6$ tertiary alkyl group attached through a tertiary carbon to the pyridazine ring, such as t-butyl, 1,1-dimethylethyl, 1,1-dimethylpropyl, or 1-methyl-1-ethylpropyl, and mineral acid addition salts thereof.

11 Claims, No Drawings

ANTIVIRAL PYRIDAZINE HYDRAZONES

BACKGROUND OF THE INVENTION

Likar et al., *J. Med. Chem.* 14 246 (1971) prepared several hydrazones of (6-chloro-3-pyridazinyl)hydrazine. Anong these, those hydrazones produced from acetone, cyclohexanone, acetophenone and 2-butanone (with a methyl group permissibly present in the pyridazine ring) markedly reduced the titer of influenza virus $A_2$ grown in the allantoic cavities of eggs. Activity was also shown by three compounds versus influenza $A_3$ and two compounds were active in vivo against semliki forest virus. No compound was active against herpes or polio I in cell culture. The same group reported later in Japel et al., *Il Farmaco Edizione Scientifica*, 28 116 (1973) that N-oxides of some of the same hydrazones of (6-chloro-3-pyridizanyl)hydrazines were active against egg-grown influenza $A_2$ but none were active against semliki forest virus.

The above information is also contained in Schauer et al., *Proc. Int. Congress on Chemotherapy*, 72 329 (1972).

In other reports of Schiff bases of 3-pyridazinylhydrazine, Steiner et al., *J. Med. Chem.*, 24 59 (1981) report the synthesis of (6-heteroaryl-3-pyridazinyl)hydrazones, tested as hypotensive agents; Matyeus et al., *Acta Chim. Acad. Sci. Hung.*, 106 205 (1981) report the preparation of $N^2$ derivatives of several 2-(6-chloro-3-pyridazinyl)hydrazones—biological data are not included; and Shams et al., *Ind J. Chem.*, 218 317 (1982) prepared Schiff bases of 6-phenyl-3-pyridazinylhydrazine using acetone, cyclohexanone, benzaldehyde, acetophenone and diphenyl ketone as the carbonyl reactants—the compounds were prepared for use in therapy or plant growth regulation.

None of the above references indicate that excellent antiviral activity would be found in hydrazones of 6-tertiary alkyl-3-pyridazinylhydrazines, nor is the synthesis of such compounds for any purpose suggested by the cited art.

SUMMARY OF THE INVENTION

This invention provides pyridazinyl hydrazones of the formula

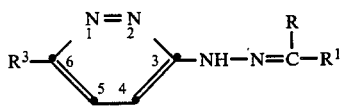

wherein when taken singly, R is H, $CH_3$ or $C_2H_5$; and $R^1$ is thienyl, halothienyl, pyridyl, methylthienyl, furyl, indolyl, tolyl, xylyl, biphenyl, $C_1$-$C_4$ alkoxyphenyl, 1-adamantyl and, when R is other than H, methyl; R and $R^1$ taken together form a 2-adamantindinyl group; and $R^3$ is a $C_4$-$C_6$ tertiary alkyl group attached through a tertiary carbon to the pyridazine ring, such as t-butyl, (1,1-dimethylethyl), 1,1-dimethylpropyl, or 1-methyl-1-ethylpropyl, and mineral acid addition salts thereof.

Compounds represented by the above formula are antiviral and antifungal agents. The compounds are particularly active against strains of influenza A. Thus, this invention also provides virucidal methods employing compounds according to the above formula as the active antiviral agents.

In the above formula, when $R^1$ is halothienyl, it can be a 2-chloro-3-thienyl, 3-chloro-2-thienyl, 2,5-dichloro-3-thienyl, 2-bromo-3-thienyl, 3-bromo-2-thienyl, 5-chloro-2-thienyl, 5-bromo-2-thienyl and the like. When $R^1$ is thienyl, it can be 2-thienyl or 3-thienyl. When $R^1$ is pyridyl, it can be 2-pyridyl, 3-pyridyl or 4-pyridyl. When $R^1$ is furyl, it can be 2-furyl or 3-furyl. When $R^1$ is halophenyl, it can be 2-chlorophenyl, 4-bromophenyl, 2,5-dichlorophenyl, 2,4-dibromophenyl, 3,4-dichlorophenyl, 2,6-dichlorophenyl, 4-fluorophenyl, 4-iodophenyl, 2-fluorophenyl and the like. When $R^1$ is $C_{1-4}$ alkoxyphenyl, it can be o, m, or p-anisyl, o, m, or p-ethoxyphenyl, o, m, or p-propoxyphenyl, o, m, or p-butoxyphenyl, 2,4-dimethoxyphenyl and the like. When $R^1$ is indolyl, the group should be a 2-indolyl or 3-indolyl derivative (substituted in the pyrrole portion of the indole). When $R^1$ is tolyl, it can be o, m, or p-tolyl. When $R^1$ is xylyl, it can be 2,4-xylyl, 2,5-xylyl, 2,6-xylyl or the like.

Pharmaceutically-acceptable acid addition salts of the bases of the above formula can be formed with strong acids such as hydrochloric, hydrobromic sulfuric, phosphoric and the like.

SPECIFIC EMBODIMENTS OF THE INVENTION

The compounds of this invention are prepared by reacting a pyridazinehydrazine of the formula

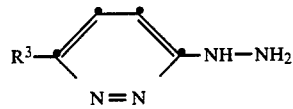

with an aldehyde or ketone of the formula

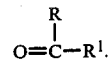

The following Example illustrates the above procedure.

EXAMPLE 1

Preparation of 1-(2-thienylethanone)[6-(1,1-dimethylethyl)-3-pyridazinyl]hydrazone Seventeen grams of 3-(1,1-dimethyllethyl)-6-chlorpyridazine were dissolved in 250 ml of isopropanol. Forty ml. of anhydrous hydrazine were added and the resulting reaction mixture heated to reflux temperature for about 12 hours. After cooling, the reaction mixture was evaporated to dryness. The resulting semi-crystalline solid was dissolved in 800 ml of $CH_2Cl_2$. The organic solution was washed with 500 ml of saturated aqueous sodium bicarbonate, and then dried. The dried organic solution was decolorized with activated charcoal and filtered. The filtrate was evaporated to dryness. A crystalline solid comprising purified 6-(1,1-dimethylethyl)-3-pyridazinylhydrazine was obtained which melted at 96°-98° C. after recrystallization from hexane/ethyl acetate; yield=8.1 g (48%).

Analysis: Calc.: C, 57.81; H, 8.49; N, 33.70; Found: C, 58.02; H, 8.22; N, 33.43.

A solution was prepared from 1.66 g. of 6-(1,1-dimethylethyl)-3-pyridazinylhydrazine and 1.26 g. of 2-acetylthiophene in 150 ml of toluene, and 150 mg of p-toluenesulfonic acid were added. The reaction mixture was vigorously refluxed in an apparatus equipped with a Dean-Stark trap. When the theoretical quantity of water had accumulated (about 2 hours), a solid, the p-toluene sulfonate salt of 1-(2-thienyl)ethanone[6-(1,1-dimethylethyl-3-pyridazinyl]hydrazone, was separated and was removed by filtration. The filtrate was evaporated to dryness in vacuo and the residual oil chromatographed over silica using $CH_2Cl_2$ containing increasing amounts (5–10%) of ethyl acetate as the eluant. Fractions shown by TLC to contain the desired material were combined and the solvent evaporated therefrom to yield 2.78 g of solid 1-(2-thienyl)ethanone[6-(1,1-dimethylethyl)-3-pyridazinyl]hydrazone.

Analysis: Calc.: C, 61.28; H, 6.61; N, 20.42; S, 11.69; Found: C, 61.20; H, 6.59; N, 20.22; S, 11.45.

Other compounds prepared from 1-[6-(1,1-dimethylethyl)-3-pyridazinyl]hydrazine include; from 1.66 g of 3-methyl-2-acetythiophene, 1-(3-methyl-2-thienyl)ethanone[6-(1,1-dimethylethyl)-3-pyridazinyl]hydrazone, yield=1.27 g.

Analysis: Calc.: C, 62.47; H, 6.99; N, 19.43; S, 11.12; Found: C, 61.35; H, 6.60; N, 18.75; S, 11.11.

Hydrochloride salt: mp=170°–172° C.

Analysis: Calc: C, 55.46; H, 6.52; N, 17.25; Cl, 9.87; S, 10.91; Found: C, 55.38; H, 6.36; N, 17.13; Cl, 11.01; S, 11.07.

from 1.66 g of 3-acetylthiophene 2.24 g of 1-(3-thienyl)ethanone[6-(1,1-dimethylethyl)-3-pyridazinyl]hydrazone; m.p.=143°–145° C.

Analysis: Calc.: C, 61.28; H, 6.61; N, 20.42; S, 11.69; Found: C, 61.54; H, 6.41; N, 20.76; S, 11.40.

from 2.9 g of indole-3-carboxaldehyde, 5.4 g (92.2% yield) of 1H-indole-3-carboxaldehyde[6-(1,1-dimethylethyl)-3-pyridazinyl]hydrazone; mp=242°–244° C.

Analysis: Calc.: C, 69.58; H, 6.53; N, 23.88; Found: C, 69.98; H, 6.26; N, 23.64.

from 1.6 g of 3-acetylindole, 2.4 g (80% yield) of 1-(1H-3-indolyl)ethanone[6-(1,1-dimethylethyl)-3-pyridazinyl]hydrazone; m.p.=231°–232° C.

Analysis: Calc.: C, 70.33; H, 6.89; N, 22.78; Found: C, 70.52; H, 6.91; N, 22.54.

from 1.21 g of 4-acetylpyridine, 1.68 g (62% yield) of 1-(4-pyridyl)ethanone[6-(1,1-dimethylethyl)-3-pyridazinyl]hydrazone; mp=198°–200° C.

Analysis: Calc.: C, 66.89; H, 7.11; N, 26.00; Found: C, 66.84; H, 6.88; N, 25.80.

from 1.21 g of 3-acetylpyridine; 1.85 g (69% yield) of 1-(3-pyridyl)ethanone[6-(1,1-dimethylethyl)-3-pyridazinyl]hydrazone.

Analysis: Calc.: C, 71.61; H, 7.51; N, 20.88; Found: C, 71.35; H, 7.36; N, 20.93.

from 1.54 g of p-chloroacetophenone, 1.75 g of 1-(4-chloro)phenylethanone[6-(1,1-dimethylethyl)-3-pyridazinyl]hydrazone.

Analysis: Calc.: C, 63.49; H, 6.32; N, 18.50; Cl, 11.71; Found: C, 63.33; H, 6.21; N, 18.26; Cl, 11.64.

from 1.54 g of m-chloroacetophenone, 2.12 g of 1-(3-chloro)phenylethanone[6-(1,1-dimethylethyl)-3-pyridazinyl]hydrazone.

Analysis: Calc.: C, 63.42; H, 6.32; N, 18.50; Cl, 11.71; Found: C, 63.37; H, 6.49; N, 18.43; Cl, 11.91.

from 1.54 g of o-chloroacetophenone, 2.35 g (78% yield) of 1-(2-chloro)phenylethanone[6-(1,1-dimethylethyl)-3-pyridazinyl]hydrazone.

Analysis: Calc.: C, 63.42; H, 6.32; N, 18.50; Cl, 11.71; Found: C, 63.48; H, 6.24; N, 18.52; Cl, 11.95.

from acetophenone, 1-phenylethanone[6-(1,1-dimethylethyl)-3-pyridazinyl]hydrazone.

Analysis: Calc.: C, 71.61; H, 7.51; N, 20.88; Found: C, 71.35; H, 7.36; N, 20.93.

The following compounds were prepared from [6-(1-methyl-1-ethyl)propyl-3-pyridazinyl)hydrazine; 1-(3-bromo)phenylpropanone[6-(1-methyl-1-ethylpropyl)-3-pyridazinyl]hydrazone.

Analysis: Calc.: C, 58.61; H, 6.47; N, 14.39; Found: C, 58.63; H, 6.45; N, 14.32.

1-(4-bromo)phenylpropanone[6-(1-methyl-1-ethylpropyl)-3-pyridazinyl]hydrazone.

Analysis: Calc.: C, 58.61; H, 6.48; N, 14.39; Found: C, 59.45; H, 6.47; N, 13.11.

4-butoxybenzaldehyde[6-(1-methyl-1-ethylpropyl)-3-pyridazinyl]hydrazine. mp=153°–155° C.

Analysis: Calc.: C, 71.15; H, 8.53; N, 15.80; Found: C, 70.46; H, 8.53; N, 16.55.

2,5-dimethylbenzaldehyde[6-(1-methyl-1-ethylpropyl)-3-pyridazinyl]hydrazone.

Analysis: Calc.: C, 73.51; H, 8.44; N, 18.05; Found: C, 73.55; H, 8.31; N, 17.94.

2,4-dimethylbenzaldehyde[6-(1-methyl-1-ethylpropyl)-3-pyridazinyl]hydrazone, mp=175°–177° C.

Analysis: Calc.: C, 66.64; H, 7.65; N, 16.36; Found: C, 66.57; H, 7.49; N, 16.18.

2,4-dimethoxybenzaldehyde[6-(1-methyl-1-ethylpropyl)-3-pyridazinyl]hydrazone. mp=216°–218° C.

Analysis: Calc.: C, 66.64; H, 7.65; N, 16.36; Found: C, 66.57; H, 7.49; N, 16.18.

3-bromobenzaldehyde[6-(1-methyl-1-ethylpropyl)-3-pyridazinyl]hydrazone. mp=180°–182° C.

Analysis: Calc.: C, 56.52; H, 5.86; N, 15.51; Found: C, 56.63; H, 5.89; N, 15.33.

3,5-dichlorobenzaldehyde[6-(1-methyl-1-ethylpropyl)-3-pyridazinyl]hydrazone. mp=257°–259° C.

Analysis: Calc.: C, 58.13; H, 5.74; N, 15.95; Found: C, 58.34; H, 5.70; N, 16.19.

3,5-dimethylbenzaldehyde[6-(1-methyl-1-ethylpropyl)-3-pyridazinyl]hydrazone. m.p.=136°–138° C.

Analysis: Calc.: C, 73.51; H, 8.44; N, 18.05; Found: C, 73.55; H, 8.31; N, 17.94.

2,4-dichlorobenzaldehyde[6-(1-methyl-1-ethylpropyl)-3-pyridazinyl]hydrazone. m.p. 193°–195° C.

Analysis: Calc.: C, 58.13; H, 5.74; N, 15.95; Found: C, 58.11; H, 5.46; N, 15.87.

2-chlorobenzaldehyde[6-(1-methyl-1-ethylpropyl)-3-pyridazinyl]hydrazone. m.p.=182°–184° C.

Analysis: Calc.: C, 64.45; H, 6.68; N, 17.68; Found: C, 64,40; H, 6.45; N, 17.57.

4-chlorobenzaldehyde[6-(1-methyl-1-ethylpropyl)-3-pyridazinyl]hydrazone. m.p.=202°–204° C.

Analysis: Calc.: C. 64.45; H, 6.68; N, 17.68; Found: C, 64.47; H, 6.45; N, 17.49.

1-(2-thienyl)ethanone[6-(1-methyl-1-ethylpropyl)-3-pyridazinyl]hydrazone.

Analysis: Calc.: C, 63.54; H, 7.33; N, 18.52; Found: C, 62.47; H, 6.83; N, 17.78.

1-(3-pyridyl)ethanone[6-(1-methyl-1-ethylpropyl)-3-pyridazinyl]hydrazone.

Analysis: Calc.: C, 68.66; H, 7.80; N, 23.55; Found: C, 68.81; H, 6.76; N, 22.58.

1-(2,5-dichloro-3-thienyl)ethanone[6-(1-methyl-1-ethylpropyl)-3-pyridazinyl]hydrazone.

Analysis: Calc.: C, 51.75; H, 5.43; N, 15.09; Found: C, 51.52; H, 5.44; N, 14.83.

1-(3-Thienyl)ethanone[6-(1-methyl-1-ethylpropyl)-3-pyridazinyl]hydrazone.

Analysis: Calc.: C, 63.54; H, 7.33; N, 18.52; Found: C, 63.42; H, 7.10; N, 18.42.

3-dichlorobenzaldehyde[6-(1-methyl-1-ethylpropyl)-3-pyridazinyl]hydrazone. m.p.=179°-181° C.

Analysis: Calc.: C, 64.55; H, 6.68; N, 17.68; Found: C, 64.28; H, 6.63; N, 17.52.

1-(2-thienyl)propanone[6-(1-methyl-1-ethylpropyl)-3-pyridazinyl]hydrazone.

Analysis: Calc.: C, 64.52; H, 7.64; N, 17.70; Found: C, 65.02; H, 7.00; N, 16.90.

1-(4-phenylphenyl)ethanone[6-(1-methyl-1-ethylpropyl)-3-pyridazinyl]hydrazone.

Analysis: Calc.: C, 77.38; H, 7.58; N, 15.04; Found: C, 77.13; H, 7.34; N, 14.81.

1-(5-chloro-2-thienyl)ethanone[6-(1-methyl-1-ethylpropyl)-3-pyridazinyl]hydrazone.

Analysis: Calc.: C, 57.04; H, 6.28; N, 16.63; Found: C, 56.49; H, 5.61; N, 15.61.

1-(5-bromo-2-thienyl)ethanone[6-(1-methyl-1-ethylpropyl)-3-pyridazinyl]hydrazone.

Analysis: Calc.: C, 50.40; H, 5.55; N, 14.69; Found: C, 50.64; H, 5.69; N, 14.73.

The following additional compounds were prepared.

1-(1-adamantyl)ethanone[6-(1,1-dimethylethyl)-3-pyridazinyl]hydrazone.

Analysis: Calc.: C, 73.58; H, 9.26; N, 17.16; Found: C, 73.78; H, 9.29; N, 17.05.

2-adamantanone[6-(1,1-dimethylethyl)-3-pyridazinyl]hydrazone. m.p.=180°-182° C.

Analysis: Calc.: C, 72.20; H, 9.09; N, 18.71; Found: C, 72.38; H, 9.17; N, 19.00.

2-propanone[6-(1,1-dimethylethyl)-3-pyridazinyl]hydrazone. m.p.=120°-122° C.

Analysis: Calc.: C, 64.05; H, 8.80; N, 27.16; Found: C, 63.83; H, 8.53; N, 26.91.

2-propanone[6-(1,1-dimethylpropyl)-3-pyridazinyl]hydrazone; m.p.=85°-86° C.

Analysis: Calc.: C, 65.42; H, 9.15; N, 25.43; Found: C, 65.69; H, 9.09; N, 25.47.

As previously stated, the compounds of this invention according to formula 1 are antiviral and antifungal agents. The compounds exhibit their antiviral activity both in vitro and in vivo. Their in vivo activity against influenza A Ann Arbor strain is particularly well-documented. The test procedure was carried out as follows. Groups of eighteen CD-1 mice were challenged with a predetermined dose of influenza A Ann Arbor strain. A predetermined dose of the drug was also administered and one group which was given vehicle alone served as a control.

First, a survival index (SI) was calculated at each drug dosage as follows.

$$S.I. \text{ for Day } X = (X - 1)\frac{\text{no. of control animals dying on day } X - 1}{\text{total no. of control animals}} + SI \text{ for day } X - 1$$

where X is a number less than 11. Survivors are those living at day 11.

Next a comparison with the control group is calculated by the following formula where p=percent of maximum.

$$P = \frac{SI \text{ treated} - SI \text{ controls}}{SI \text{ survivors} - SI \text{ control}} \times 100$$

This percent of maximum is then allocated to a relative activity index RA as follows:

| P | RA | |
|---|---|---|
| 10% or less = | 1 | (borderline) |
| 20-40% = | 2 | (slightly active) |
| 40-60% = | 3 | (moderately active) |
| 60-80% = | 4 | (good activity) |
| 80-100% = | 5 | (very active) |

The following Table gives RA values for compounds of this invention.

TABLE

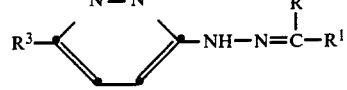

| R | R¹ | R³ | RA |
|---|---|---|---|
| Me | 2-thienyl | t-Bu | 3.0 |
| Me | 3-thienyl | t-Bu | 3.5 |
| H | 3-indolyl | t-Bu | 4.5 |
| Me | 3-indolyl | t-Bu | |
| Me | 4-pyridyl | t-Bu | 4.0 |
| Me | 3-pyridyl | t-Bu | 4.0 |
| Me | 4-chlorophenyl | t-Bu | 2.0 |
| Me | 3-chlorophenyl | t-Bu | 2.0 |
| Me | 2-chlorophenyl | t-Bu | 2.5 |
| Me | phenyl | t-Bu | 3.0 |
| Et | 3-bromophenyl | MEP | 1.5 |
| Et | 4-bromophenyl | MEP | 3.0 |
| H | 4-n-butoxyphenyl | MEP | 1.0 |
| H | 2,5-xylyl | MEP | 2.0 |
| H | 2,4-xylyl | MEP | 1.0 |
| H | 2,4-dimethoxyphenyl | MEP | 2.0 |
| H | 3-bromophenyl | MEP | 0.5 |
| H | 3,5-dichlorophenyl | MEP | 1.0 |
| H | 2,4-dichlorophenyl | MEP | 2.5 |
| H | 2-chlorophenyl | MEP | 3.0 |
| H | 4-chlorophenyl | MEP | 1.0 |
| Me | 2-thienyl | MEP | 2.5 |
| Me | 3-pyridyl | MEP | 2.5 |
| Me | 2,5-dichloro-3-thienyl | MEP | 2.5 |
| Me | 3-thienyl | MEP | 4.0 |
| H | 3-chlorophenyl | MEP | 2.5 |
| Et | 2-thienyl | MEP | 2.5 |
| Me | 5-chloro-2-thienyl | MEP | 1.0 |
| Me | 5-bromo-2-thienyl | MEP | 3.0 |
| Me | 1-adamantyl | t-Am | 0.5 |
| 2-adamantylidinyl | | t-Bu | 3.5 |
| Me | Me | t-Bu | 3.0 |
| Me | Me | t-Am | 4.0 | t-Bu = tertiary butyl; MEP = 1-methyl-1-ethylpropyl; t-Am = 1,1-dimethylpropyl.

The compounds have also shown virucidal activity in vitro against the following virus strains:
Influenza A (WSN),
Influenza A (Hong Kong),
Influenze A (Singapore).

For in vitro use, the compounds can be formulated by dissolving them in a lower alkanol, for example ethanol or methanol, or at low concentration as an emulsion in water with the use of a surface active agent. The antiviral composition containing a compound according to formula I as the active ingredient is, therefore, applied to the virus habitat in vitro, such habitats including walls of hospital rooms, laboratory benches, laboratory glassware, and the like. The compounds can also be added to tissue culture to suppress viral growth therein. For in vivo use, the compounds can be administered either parenterally or orally. For parenteral administration, as by the intraperitoneal route employed in the above experimental work, the compound may be dissolved in water containing 2% of a surface active agent, particularly an emulphor (a polyhydroxylated fatty acid). Oral administration is, of course, preferred. For such use, a compound according to formula I above is mixed with one or more standard pharmaceutically-acceptable extending media such as starch sucrose, lactose, calcium carbonate etc. and the mixture loaded into empty telescoping gelatin capsules, such that each capsule contains an amount of a compound effective to suppress the growth of influenza virus, either prospective or present. In other words, the compounds can be used prophylactically or as curative agents. Alternatively, the drug can be mixed with various excipients including starch, lubricating agents, wetting agents, etc., such as stearic acid, magnesium stearate and the like, and the mixture pressed into tablets, each tablet containing an amount of the drug effective to abort or cure an attack of influenza. Such tablets can be scored so as to provide half or quarter dosages where the drug is to be administered to children. The compounds can also be administered in solution or suspension.

Compounds represented by formula I above are administered to mammals susceptible to infection with influenza virus including horses, mice, pigs and humans. Among humans, the compounds are administered prophylactically particularly to the elderly, young children, nurses, doctors, and other hospital or public health personnel, when there is evidence of an imminent "flu" epidemic. The compounds can also be given to anyone having a known exposure to a person with "flu". It is a particular advantage of the therapeutic processes of this invention that the compounds may be administered either prophylactically or therapeutically to patients without a preliminary determination that the virus is influenza virus A strain or B strain, since the compounds are effective against both strains.

The compounds according to formula I also have antifungal activity against agriculturally important fungus diseases including apple scab and downey mildew (complete control at 25 ppm for selected compounds). For use in agriculture, the compounds of this invention may be formulated with a suitable agriculturally-acceptable carrier or diluent. Such compositions will contain from about 0.1 to about 95.0 percent by weight of the active ingredient, depending on the composition desired. Preferred formulations will contain from about 1 to about 50 percent active ingredient. Sprayable formulations are preferred, because of the rapidity and economy of application, and because the sprayed applications do not drift to untreated areas as would some formulations, for example, a dust.

Dust compositions will contain a compound according to formula I generally in an amount from about 0.1 to about 5 percent by weight. Dusts are prepared by intimately mixing and finely grinding the compound with an inert solid diluent or carrier such as ground montmorillonite clay, attapulgite clay, talc, ground volcanic rock, kaolin clay, or other inert, relatively dense, inexpensive substances.

The most convenient formulations contemplated are in the form of concentrated compositions. Such formulations are diluted with water, generally at or near the site of application and are applied by spraying the resulting water dispersion or emulsion. The diluted compositions generally will contain the active compounds in the range from about 0.1 percent to about 10 percent by weight. Water-dispersible or emulsifiable compositions may be either solids, usually known as wettable powders, or liquids, usually known as emulsifiable concentrates or aqueous suspensions.

A typical wettable powder comprises an intimate mixture of an active agent, one or more inert carriers, and one or more surfactants. The concentration of the active compound is usually from about 5 percent to about 90 percent by weight, ideally about 10 about 70 percent. The inert carrier is usually to chosen from among the attapulgite clays, the montmorillonite clays, the diatomaceous earths, the purified silicates, or other similar substances that are readily available. Effective surfactants, comprising from about 0.5 percent to about 10 percent by weight of the wettable powder, are chosen from among the sulfonated lignins, the condensed naphthalenesulfonates, the alkyl sulfates, and related materials.

A typical emulsifiable concentrate comprises from about 0.1 to about 6 pounds of an active compound per gallon of liquid, dissolved in a mixture of an organic solvent and an emulsifier. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers include ionic surfactants such as the alkylbenzenesulfonates and naphthalenesulfonates, as well as non-ionic surfactants such as alkylphenol adducts of polyoxyethylene, and are used at similar percentages as for wettable powders.

Solid, granular compositions are convenient for the application of compounds employed by this invention to the soil. Granules comprise a compound dispersed on a granular inert carrier such as coarsely ground clay of from about 0.1 to about 3 mm. particle size. The compound is most conveniently applied to the clay by dissolving it in an inexpensive solvent such as acetone and applying the solution to the sized clay in an appropriate solids mixer. The solvent is then removed by evaporation or the like.

The formulated compounds are applied to plants and to the locus when the plants are growing in the manners conventional in agricultural chemistry. Sprayable compositions are easily applied by any of many types of sprayers available to the art. Selfpropelled, tractor-mounted, and towed spray devices which apply the water-dispersed formulations through calibrated atomizing nozzles are available and effective. Metering applicators are also available which can apply accurately measured quantities of granular compositions to the locus to be treated. The operator of the application equipment need only take care to adjust the equipment to apply an amount of the water-dispersed or granular formulation which supplies the desired application rate of the compound, and to apply the amount uniformly to the plants to be treated.

I claim:

1. A compound of the formula 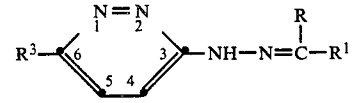 wherein when taken singly, R is H, $CH_3$ or $C_2H_5$; and $R^1$ is thienyl, halothienyl, pyridyl, methylthienyl, furyl, indolyl, tolyl, xylyl, biphenyl, $C_1$-$C_4$ alkoxyphenyl, 1-adamantyl and, when R is other than H, methyl; R and R¹ taken together form a 2-adamantindinyl group; and R³ is $C_4$–$C_6$ tertiary alkyl group attached through a tertiary carbon to the pyridazine ring and mineral acid addition salts thereof.

2. A compound according to claim 1 in which R¹ is pyridyl.

3. A compound according to claim 1 in which R¹ is thienyl or halothienyl.

4. A compound according to claim 1 in which R¹ is indolyl.

5. A compound according to claim 2, said compound being 1-(3-pyridyl)ethanone[6-(1,1-dimethylethyl)-3-pyridazinyl)hydrazone.

6. A compound according to claim 2, said compound being 1-(4-pyridyl)ethanone[6-(1,1-dimethylethyl)-3-pyridazinyl]hydrazone.

7. A compound according to claim 3, said compound being 1-(3-thienyl)ethanone[6-(1-methyl-1-ethyl-propyl)-3-pyridazinyl]hydrazone.

8. A compound according to claim 1, said compound being 2-acetone[6-(1,1-dimethylpropyl)-3-pyridazinyl]-hydrazone.

9. A compound according to claim 4, said compound being 1H-indole-3-carboxaldehyde[6-(1,1-dimethylethyl)-3-pyridazinyl]hydrazone.

10. The method which comprises administering to mammals susceptible to infection with a virus a virucidal amount of a compound according to claim 1.

11. A process according to claim 10 in which the virus to be killed is influenza Ann Arbor Strain.

* * * * *